(12) United States Patent
Menn

(10) Patent No.: US 10,687,844 B2
(45) Date of Patent: Jun. 23, 2020

(54) CATHETER ATHERECTOR

(71) Applicant: Pavel Menn, Salem, MA (US)

(72) Inventor: Pavel Menn, Salem, MA (US)

( * ) Notice: Subject to any disclaimer, the term of this patent is extended or adjusted under 35 U.S.C. 154(b) by 0 days.

(21) Appl. No.: 16/684,373

(22) Filed: Nov. 14, 2019

(65) Prior Publication Data

US 2020/0146711 A1    May 14, 2020

Related U.S. Application Data

(60) Provisional application No. 62/767,283, filed on Nov. 14, 2018.

(51) Int. Cl.
*A61B 17/3207* (2006.01)

(52) U.S. Cl.
CPC ......... *A61B 17/320783* (2013.01); *A61B 17/320725* (2013.01); *A61B 17/320758* (2013.01); *A61B 2017/320775* (2013.01)

(58) Field of Classification Search
CPC ...... A61B 17/32002; A61B 17/320725; A61B 17/320758; A61B 17/320783; A61B 17/1637; A61B 17/164; A61B 2017/320775; A61B 2017/320024
See application file for complete search history.

(56) References Cited

U.S. PATENT DOCUMENTS

| | | | | |
|---|---|---|---|---|
| 5,100,426 A | * | 3/1992 | Nixon | A61B 17/320758 604/22 |
| 5,116,350 A | * | 5/1992 | Stevens | A61B 17/320758 606/159 |
| 5,632,755 A | * | 5/1997 | Nordgren | A61B 17/32075 604/22 |
| 6,156,046 A | * | 12/2000 | Passafaro | A61B 17/221 128/898 |
| 9,675,376 B2 | * | 6/2017 | To | A61B 17/320708 |
| 2004/0006358 A1 | * | 1/2004 | Wulfman | A61B 5/061 606/167 |
| 2006/0229646 A1 | * | 10/2006 | Sparks | A61B 17/320758 606/159 |
| 2012/0109171 A1 | * | 5/2012 | Zeroni | A61B 17/320758 606/159 |
| 2016/0374717 A1 | * | 12/2016 | Steele | A61B 17/320758 606/159 |
| 2017/0000518 A1 | * | 1/2017 | Smith | A61B 17/320758 |
| 2019/0290313 A1 | * | 9/2019 | Herrin | A61B 17/3201 |

* cited by examiner

*Primary Examiner* — Sarah W Aleman
(74) *Attorney, Agent, or Firm* — Daniel N. Smith

(57) ABSTRACT

An improved catheter atherector for shaving, cutting, and emulsifying accumulated plaque into fine particles, and removing the particles from blood vessel walls without cutting or permanently stretching the walls, and without substantially blocking the blood flow through the vessel during plaque removal operation. The catheter atherector includes an emulsification reduction sphere and extraction wire that rotate and move axially inside the vessel to engage the occlusive material. Emulsified occlusive reduced plaque material and blood only flow in a proximal direction into a catheter lumen. The operation of the device does not substantially disrupt blood pressure within the blood vessel.

19 Claims, 17 Drawing Sheets

CATHETER ATHERECTOR

CROSS REFERENCE TO RELATED APPLICATION

This application claims the benefit of U.S. Provisional Patent Application No. 62/767,283 filed on Nov. 14, 2018, the contents of which are incorporated herein by reference.

FIELD OF THE INVENTION

This invention relates to an improved catheter atherector for shaving, cutting, and emulsifying accumulated plaque from blood vessel walls into small particles, without cutting or permanently stretching the walls, and without substantially blocking the blood flow through the vessel during plaque removal operation, with removing the plaque from cardiovascular system without allowing it to flow downstream.

BACKGROUND OF INVENTION

Atherosclerosis is a form of arteriosclerosis in which plaque accumulates in an arterial vessel and the artery wall thickens as a result of invasion and accumulation of white blood cells on the inner artery vessel walls. These plaque accumulations contain both living, active WBCs (producing inflammation) and remnants of dead cells, including cholesterol and triglycerides. The remnants eventually include calcium and other crystallized materials, to form plaque. The plaque reduces the elasticity of the artery vessel walls. It is commonly referred to as a "hardening" or furring of the arteries.

Over time these plaques can become large enough to reduce or occlude blood flow through the vessels, leading to symptoms of low blood flow. To treat this disease blood flow must be restored through the vessel, by removing or reducing the size of these plaques.

Various types of atherectomy catheters and devices have been used to remove unwanted plaque from blood vessels to open the vessel and improve blood flow. Atherectomy catheters and devices are intravascular devices that mechanically remove plaque from the artery vessel walls.

However, atherectomy catheters and devices often undesirably cut, perforate, tear and stretch the vessel, causing scar formation. Such scar tissue causes inflammation, stenosis and blocks flow in the vessel and often needs to be removed. Furthermore, atherectomy catheters often run at high speeds causing temperature and causing damage to the vessels. Finally, atherectomy catheters block arterial blood flow completely during plaque removal, resulting in high vessel blood pressure, and posing a danger to the patient.

It is therefore desirable to provide improved atherectomy catheters and methods. An atherectomy catheter that efficiently removes plaque from artery vessel walls, without cutting or permanently stretching the walls. Devices that do not reduce blood flow during operating.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a device configured to remove occlusive material from a vessel, comprising: a catheter with a hollow elongated lumen, a proximal opening, and a distal opening, an emulsification reduction of plaque particles sphere within the distal opening of the catheter, wherein the emulsification reduction of plaque particles sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved sharp bottom surface extending inward; an opening on the emulsification reduction of plaque particles sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification of plaque particles sphere; wherein the emulsification reduction of plaque particles sphere and the emulsification-extraction wire are configured to each independently rotate in opposite directions and move axially inside the vessel to engage the occlusive material; wherein the plurality of protrustions shave and scoop the occlusive material into the plurality of occlusive material cutters for emulsification into reduced particles, and the plurality of protrusions are configured such that the movement of the plurality of protrusions does not pierce or cut the vessel wall; wherein the distal sharp tips of each protrusion shave the occlusive material into the plurality of occlusive material particles for emulsification and distal sharp tips are configured to not contact the vessel wall; and wherein the mixture of emulsified occlusive material and blood only flows in a proximal direction into the catheter lumen through the plurality of occlusive material helical walls of the extraction wire cutters, wherein the mixture of emulsified occlusive material and blood is filtered and flows back into the vessel.

The subject invention further discloses a device configured to remove occlusive material from a vessel, comprising: a catheter with a hollow elongated lumen, a proximal opening, and a distal opening, a shaving and particles sphere within the distal opening of the guide catheter, wherein the shaving and particles sphere comprises a substantially spherical shape composed of a plurality of alternating, adjacent protrusions and slots, wherein each protrusion comprises a substantially smooth, curved surface extending outward, and distal sharp blades at the tip, and each slot comprises a substantially smooth, curved surface extending inward; an opening on the shaving and particles sphere into the distal opening of the catheter within the plurality of protrusions and slots; an emulsification-extraction wire contained within the lumen of catheter, wherein the emulsification-extraction wire comprises a substantially cylindrical screw helical ridged body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the shaving and particles sphere; wherein the shaving and particles sphere and the emulsification-extraction wire are configured to each independently rotate and move axially inside the vessel to engage the occlusive material; wherein the plurality of protrusions shave and scoop the occlusive material into the plurality of occlusive material slots for emulsification into reduced particles by sharp surfaces on the bottoms of the slots, and the plurality of protrusions are configured such that the movement of the plurality of protrusions does not pierce or cut the vessel wall; wherein the distal sharp edges of each protrusion shave and cut the occlusive material into the plurality of occlusive material slots for emulsification and distal sharp edges and tips are configured to not contact the vessel wall; wherein the mixture of emulsified occlusive material and blood only flows in a proximal direction into the catheter lumen through the plurality of occlusive material slots, wherein the mixture of emulsified occlusive material and blood is filtered and flows back into the vessel; and wherein during operation of the device, the device is configured such that laminar blood flow continues substantially uninterrupted in the blood vessel by flowing around the plurality of slots on the shaving and particles sphere and around the catheter within the vessel walls.

The subject invention also discloses a device configured to remove occlusive material from a vessel, comprising: a catheter with a hollow elongated lumen, a proximal opening, and a distal opening, an emulsification reduction sphere within the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp edges and tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification sphere; wherein the emulsification reduction sphere and the emulsification-extraction wire are configured to each independently rotate in opposite directions and together move axially inside the vessel to engage the occlusive material; wherein the plurality of protrusions shave and scoop the occlusive material into the plurality of occlusive material cutters for emulsification and the plurality of protrusions are configured such that the movement of the plurality of protrusions does not pierce or cut the vessel wall; wherein the distal sharp tips of each protrusion cut the occlusive material into the plurality of occlusive material cutters for emulsification and distal sharp tips are configured to not contact the vessel wall; wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein during operation of the device, the device is configured such that it does not substantially disrupt blood flow and pressure within the blood vessel.

The subject invention further discloses an atherectomy catheter configured to remove plaque from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of plaque cutters on the distal end of the emulsification-extraction wire extending outwardly from the distal opening of the catheter, wherein the plurality of plaque cutters are contained within the plurality of protrusions on the emulsification sphere; wherein the emulsification reduction sphere and the emulsification-extraction wire each rotate in opposite directions and move together axially inside the vessel to engage the plaque; wherein the plurality of protrusions shave and scoop the plaque into the plurality of plaque cutters for emulsification and the movement of the plurality of protrusions does not pierce or cut the vessel wall; wherein the distal sharp tips of each protrusion cut the plaque into the plurality of plaque cutters for emulsification and distal sharp tips do not contact the vessel wall; and wherein the mixture of emulsified plaque and blood only flows in a proximal direction into the catheter lumen through the plurality of plaque cutters, wherein the mixture of emulsified plaque and blood is filtered and flows back into the vessel.

The subject invention discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification sphere; wherein the emulsification reduction sphere and the emulsification-extraction wire are configured to each independently rotate and move axially inside the vessel to engage the occlusive material; wherein the plurality of protrusions shave and scoop the occlusive material into the plurality of occlusive material cutters for emulsification into reduced particles, and the plurality of protrusions are configured such that the movement of the plurality of protrusions does not pierce or cut the vessel wall; wherein the distal sharp tips of each protrusion cut the occlusive material into the plurality of occlusive material cutters for emulsification and distal sharp tips are configured to not contact the vessel wall; and wherein the mixture of emulsified occlusive material and blood only flows in a proximal direction into the catheter lumen through the plurality of occlusive material cutters, wherein the mixture of emulsified occlusive material and blood is filtered and flows back into the vessel.

The subject invention further discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification sphere; wherein the emulsification reduction sphere and the emulsification-extraction wire are configured to each independently rotate and move axially inside the vessel to engage the occlusive material; wherein the plurality of protrusions shave and scoop the occlusive material into the plurality of occlusive material cutters for emulsification into reduced particles, and the plurality of protrusions are configured such that the movement of the plurality of protrusions does not pierce or cut the vessel wall; wherein the distal sharp tips of each protrusion cut the occlusive material into the plurality of occlusive material cutters for emulsification and distal sharp tips are configured to not contact the vessel wall; wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein during operation of the device, the device is configured such that laminar blood flow continues substantially uninterrupted in the blood vessel by flowing around the plurality of slots on the emulsification reduction sphere and around the catheter within the vessel walls.

The subject invention also discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification sphere; wherein the emulsification reduction sphere and the emulsification-extraction wire are configured to each independently rotate and move axially inside the vessel to engage the occlusive material; wherein the plurality of protrusions shave and scoop the occlusive material into the plurality of occlusive material cutters for emulsification and the plurality of protrusions are configured such that the movement of the plurality of protrusions does not pierce or cut the vessel wall; wherein the distal sharp tips of each protrusion cut the occlusive material into the plurality of occlusive material cutters for emulsification and distal sharp tips are configured to not contact the vessel wall; wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein during operation of the device, the device is configured such that it does not substantially disrupt blood pressure within the blood vessel.

The subject invention discloses an atherectomy catheter configured to remove plaque from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen, a plurality of plaque cutters on the distal end of the emulsification-extraction wire extending outwardly from the distal opening of the catheter, wherein the plurality of plaque cutters are contained within the plurality of protrusions on the emulsification sphere; wherein the emulsification reduction sphere and the emulsification-extraction wire each rotate and move axially inside the vessel to engage the plaque, wherein the plurality of protrustions shave and scoop the plaque into the plurality of plaque cutters for emulsification and the movement of the plurality of protrusions does not pierce or cut the vessel wall; wherein the distal sharp tips of each protrusion cut the plaque into the plurality of plaque cutters for emulsification and distal sharp tips do not contact the vessel wall; wherein the mixture of emulsified plaque and blood only flows in a proximal direction into the catheter lumen through the plurality of plaque cutters, wherein the mixture of emulsified plaque and blood is filtered and flows back into the vessel;

and wherein during operation of the device, laminar blood flow continues substantially interrupted in the blood vessel by flowing around the plurality of slots on the emulsification reduction sphere and around the catheter within the vessel walls.

The subject invention also discloses an atherectomy catheter configured to remove plaque from a vessel, comprising: a catheter with a hollow elongated lumen, a proximal opening, and a distal opening, an emulsification reduction sphere surrounding the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved surface extending inward; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen, a plurality of plaque cutters on the distal end of the emulsification-extraction wire extending outwardly from the distal opening of the catheter, wherein the plurality of plaque cutters are contained within the plurality of protrusions on the emulsification sphere; wherein the emulsification reduction sphere and the emulsification-extraction wire each rotate and move axially inside the vessel to engage the plaque, wherein the plurality of protrustions shave and scoop the plaque into the plurality of plaque cutters for emulsification and the movement of the plurality of protrustions does not pierce or cut the vessel wall; wherein the distal sharp tips of each protrusion cut the plaque into the plurality of plaque cutters for emulsification and distal sharp tips do not contact the vessel wall; wherein the mixture of emulsified plaque and blood only flows in a proximal direction into the catheter lumen through the plurality of plaque cutters, wherein the mixture of emulsified plaque and blood is filtered and flows back into the vessel; and wherein during operation of the device does not substantially disrupt blood pressure within the blood vessel.

The subject invention discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a plurality of alternating, adjacent protrusions and slots, wherein each protrusion comprises a substantially smooth, curved surface and a distal sharp tip, and each slot comprises a substantially smooth, curved surface; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body; an occlusive material cutter on the distal end of the emulsification-extraction wire extending outwardly from the distal opening of the catheter, wherein the occlusive material cutter is contained within the plurality of protrusions on the emulsification sphere; wherein the emulsification reduction sphere and the emulsification-extraction wire each rotate and move axially inside the vessel to engage the occlusive material, wherein the plurality of protrustions shave and scoop the occlusive material into the occlusive material cutter for emulsification and the movement of the plurality of protrusions does not pierce or cut the vessel wall; wherein the distal sharp tips of each protrusion cut the occlusive material into the occlusive material cutter for emulsification and distal sharp tips do not contact the vessel wall; and wherein the mixture of emulsified occlusive material and blood only flows in a proximal direction into the catheter lumen through the plurality of occlusive material cutters, wherein the mixture of emulsified occlusive material and blood is filtered and flows back into the vessel.

The subject invention discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a plurality of alternating, adjacent protrusions and slots, wherein each protrusion comprises a substantially smooth, curved surface and a distal sharp tip, and each slot comprises a substantially smooth, curved surface; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body; an occlusive material cutter on the distal end of the emulsification-extraction wire extending outwardly from the distal opening of the catheter, wherein the occlusive material cutter is contained within the plurality of protrusions on the emulsification sphere; wherein the emulsification reduction sphere and the emulsification-extraction wire each rotate and move axially inside the vessel to engage the occlusive material, wherein the plurality of protrustions shave and scoop the occlusive material into the occlusive material cutter for emulsification and the movement of the plurality of protrusions does not pierce or cut the vessel wall; wherein the distal sharp tips of each protrusion cut the occlusive material into the occlusive material cutter for emulsification and distal sharp tips do not contact the vessel wall; and wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein during operation of the device, laminar blood flow continues substantially interrupted in the blood vessel by flowing around the plurality of slots on the emulsification reduction sphere and around the catheter within the vessel walls.

The subject invention further discloses a device configured to remove occlusive material from a vessel, comprising: a catheter with a hollow elongated lumen, a proximal opening, and a distal opening, an emulsification reduction sphere surrounding the distal opening of the catheter, wherein the emulsification reduction sphere comprises a plurality of alternating, adjacent protrusions and slots, wherein each protrusion comprises a substantially smooth, curved surface and a distal sharp tip, and each slot comprises a substantially smooth, curved surface; an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body; an occlusive material cutter on the distal end of the emulsification-extraction wire extending outwardly from the distal opening of the catheter, wherein the occlusive material cutter is contained within the plurality of protrusions on the emulsification sphere; wherein the emulsification reduction sphere and the emulsification-extraction wire each rotate and move axially inside the vessel to engage the occlusive material, wherein the plurality of protrusions shave and scoop the occlusive material into the occlusive material cutter for emulsification and the movement of the plurality of protrusions does not pierce or cut the vessel wall; wherein the distal sharp tips of each protrusion cut the occlusive material into the occlusive material cutter for emulsification and distal sharp tips do not contact the vessel wall; and wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein operation of the device does not substantially disrupt blood pressure within the blood vessel.

In embodiments of the subject invention, the emulsification reduction sphere rotates at a rate of 60 rpm to 3000 rpm.

In embodiments of the subject invention, the blood flow from the device is collected for medical evaluation and disposal.

In additional embodiments of the subject invention, the emulsification reduction sphere is expandable and retractable.

In other embodiments of the subject invention, the emulsification reduction sphere comprises different sized diameters for different diameters of arteries.

In embodiments of the subject invention, the rotational and axial movement of the emulsification-extraction wire is independent from the rotational and axial movement of the emulsification sphere.

In further embodiments of the subject invention, the emulsification-extraction wire rotates at a rate faster than the emulsification sphere.

In other embodiments of the subject invention, the emulsification-extraction wire rotates at a rate of 100 rpm and 5000 rpm.

In further embodiments of the subject invention, the emulsification reduction sphere comprises a diameter of 1.5 to 8 millimeters.

In additional embodiments of the subject invention, the plurality of alternating, adjacent protrusions on the emulsification reduction sphere each comprise a width of 30% to 50% of the diameter of the emulsification reduction sphere.

In other embodiments of the subject invention, the plurality of alternating, adjacent slots on the emulsification reduction sphere each comprise a width of 10% to 50% of the diameter of the emulsification reduction sphere.

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

In embodiments of the subject invention, the term "relatively" is defined as a comparison of a property, or the proportion of a property between two components.

BRIEF DESCRIPTION OF THE DRAWINGS

Advantages of the present invention will be apparent from the following detailed description of embodiments, which description should be considered in conjunction with the accompanying drawings, in which.

DETAILED DESCRIPTION OF THE EMBODIMENTS

Figure 1:
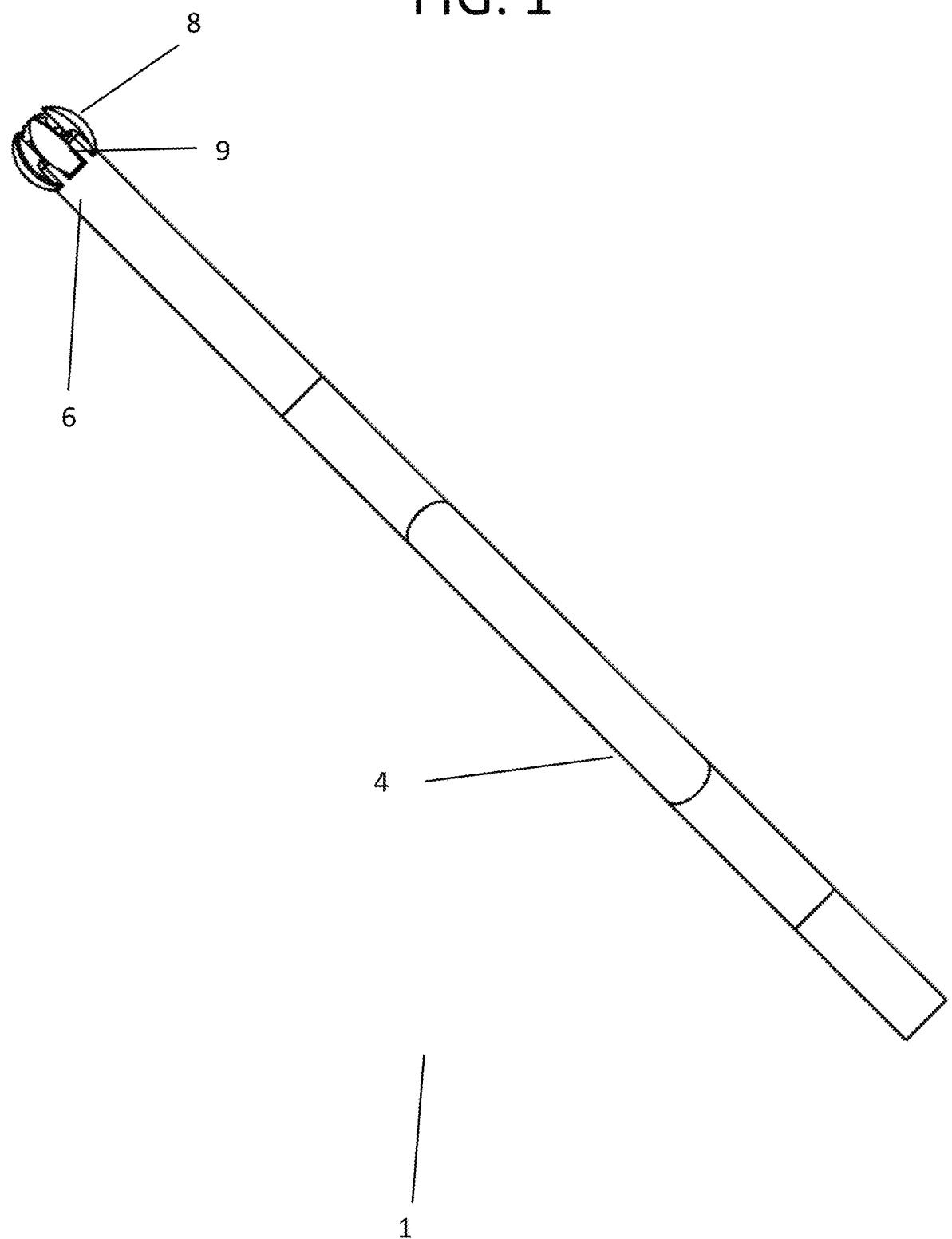
FIG. 1 illustrates a top isometric view of a catheter atherector.
Figure 2:
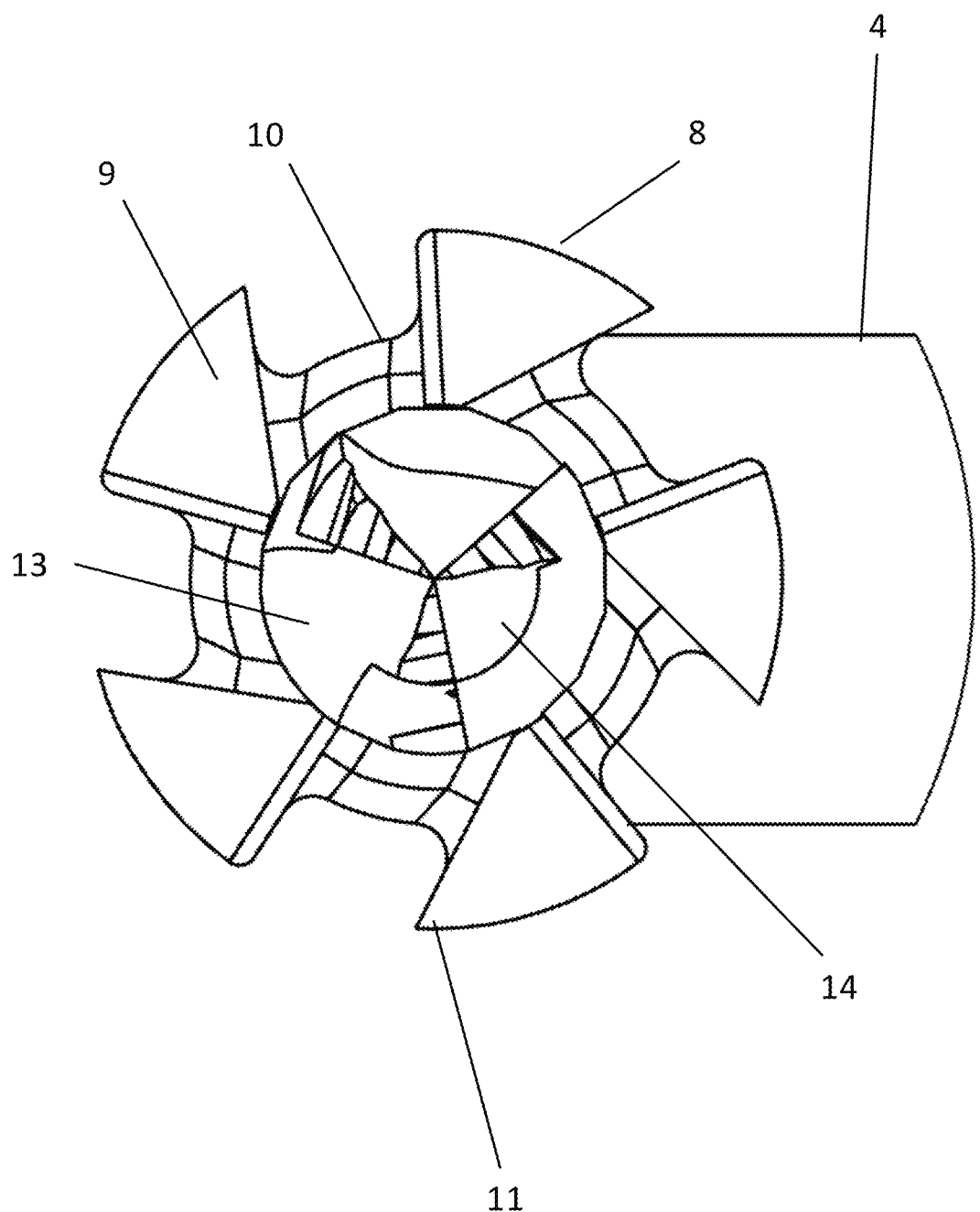
FIG. 2 illustrates a front view of a distal end of the catheter atherector.
Figure 3:
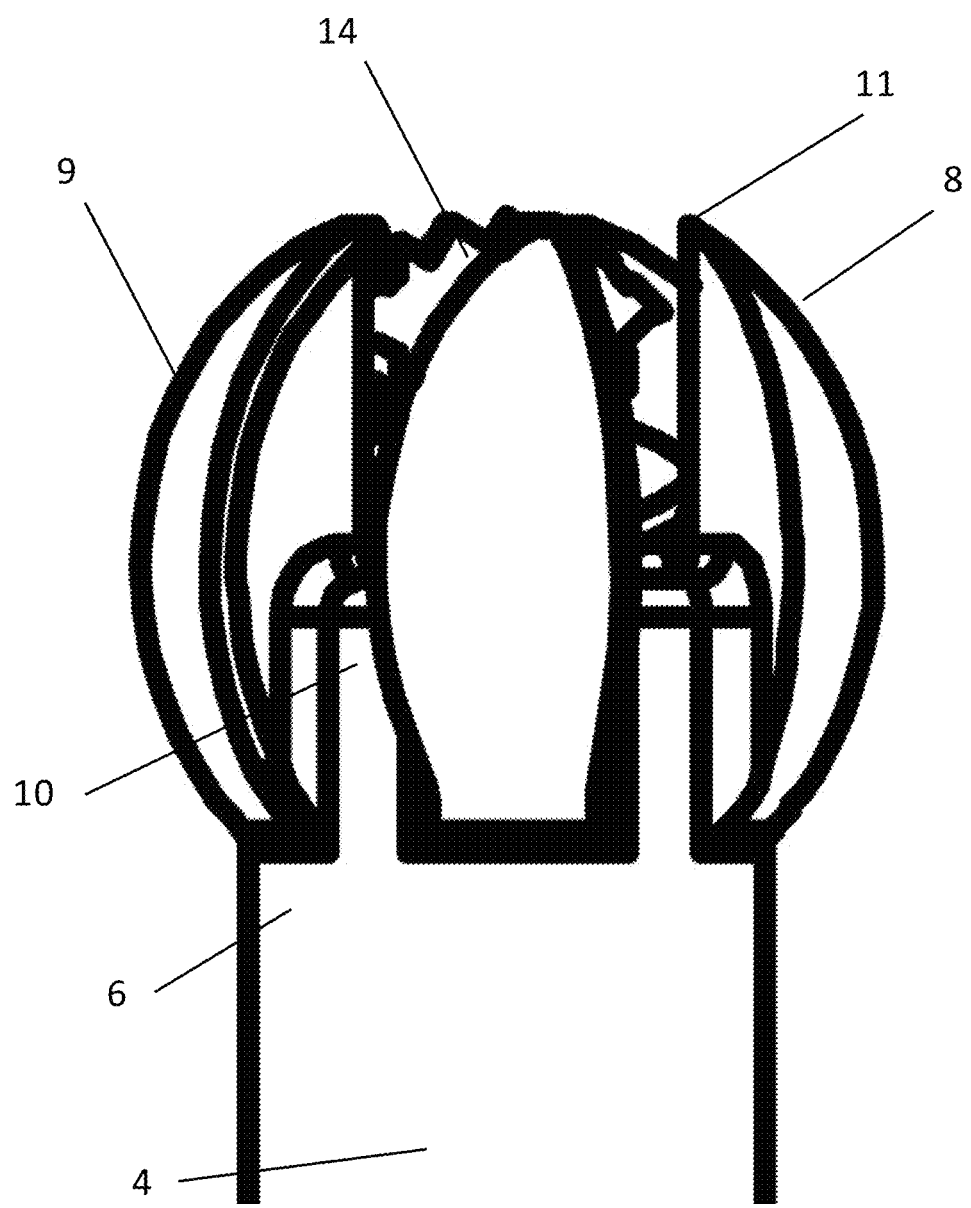
FIG. 3 illustrates a side view of the distal end of the catheter atherector.
Figure 4:
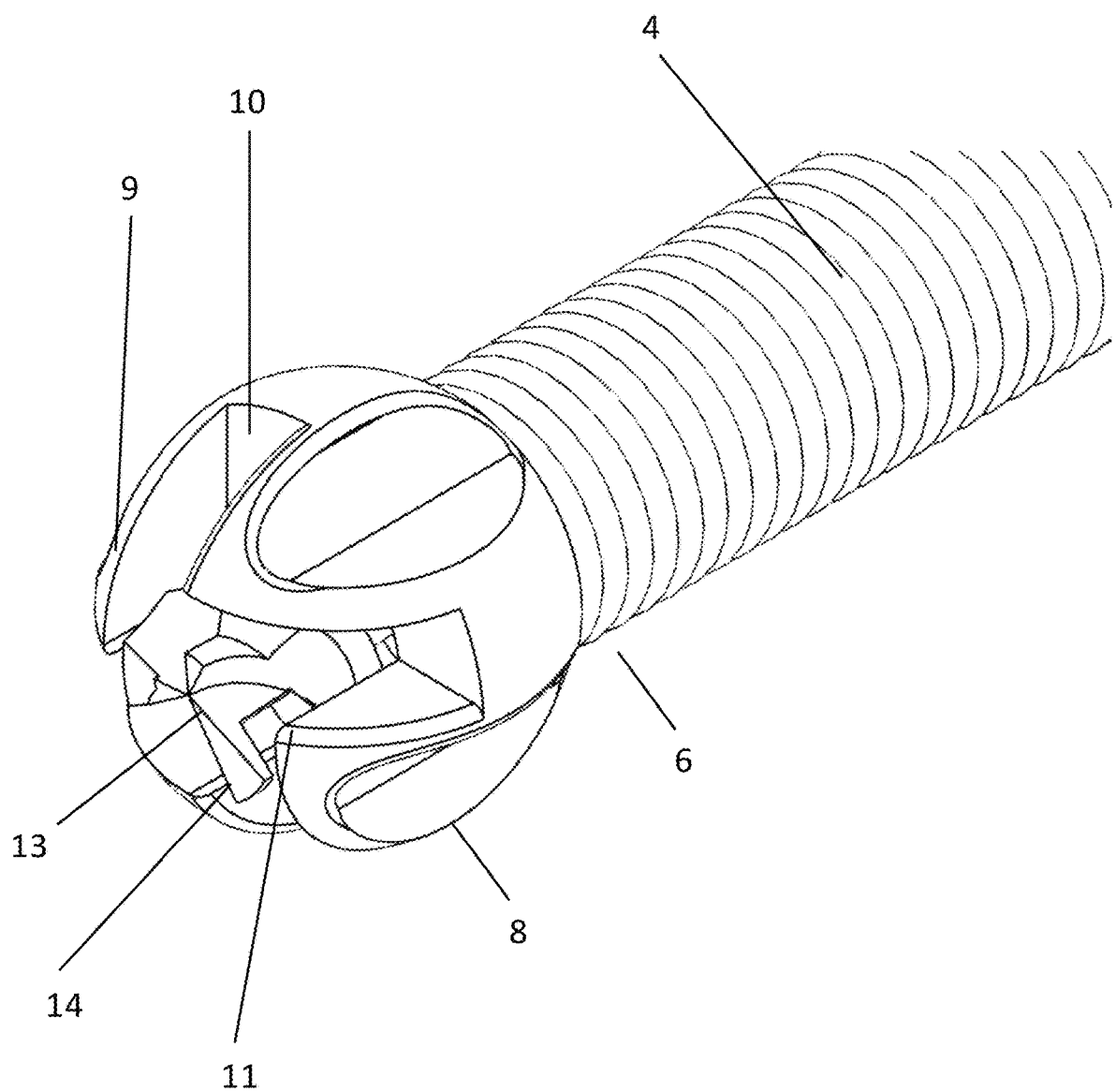
FIG. 4 illustrates a top isometric view of the distal end of the catheter atherector.
Figure 5:
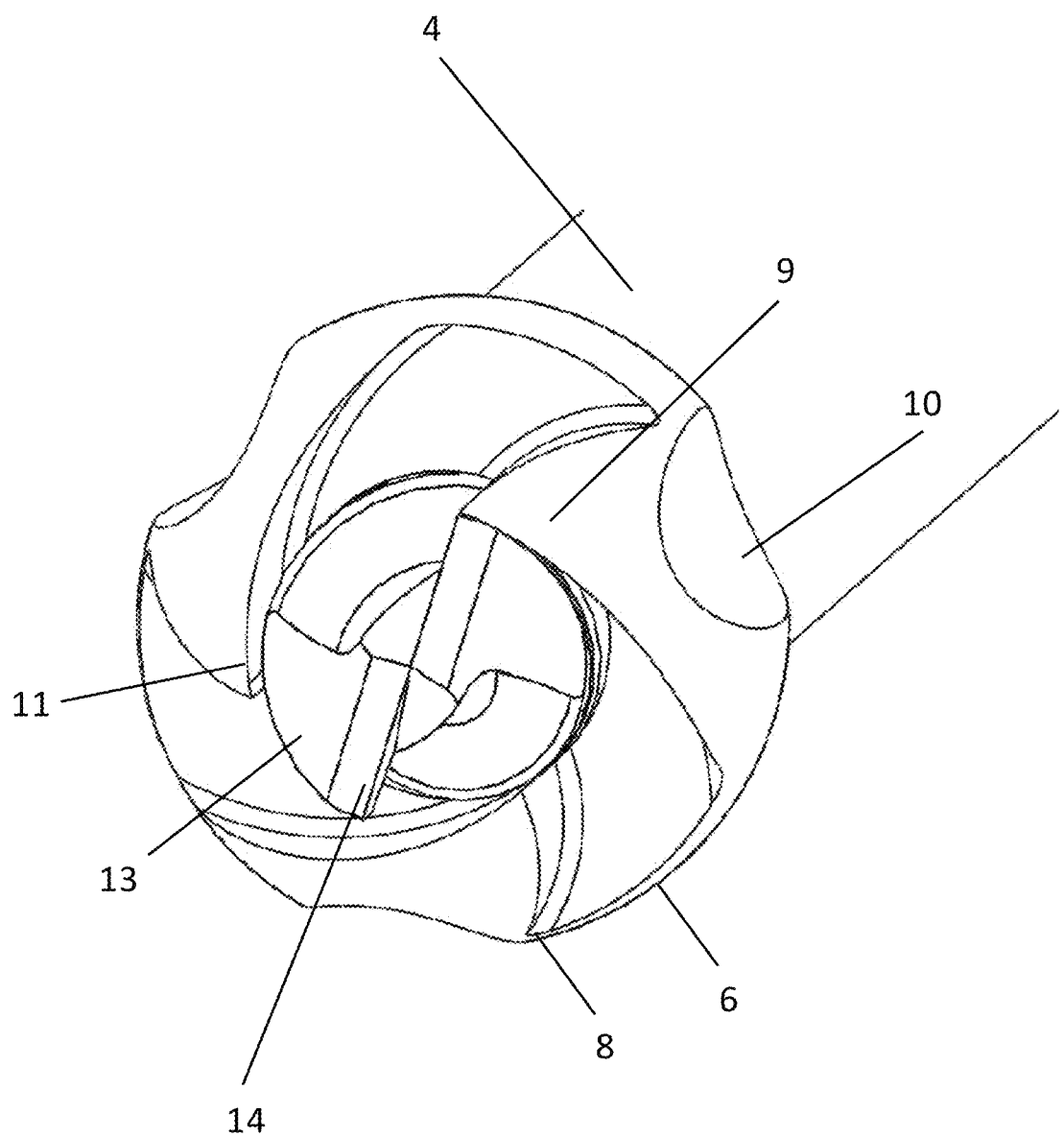
FIG. 5 illustrates a top isometric view of the distal end of another embodiment of the catheter atherector.
Figure 6:
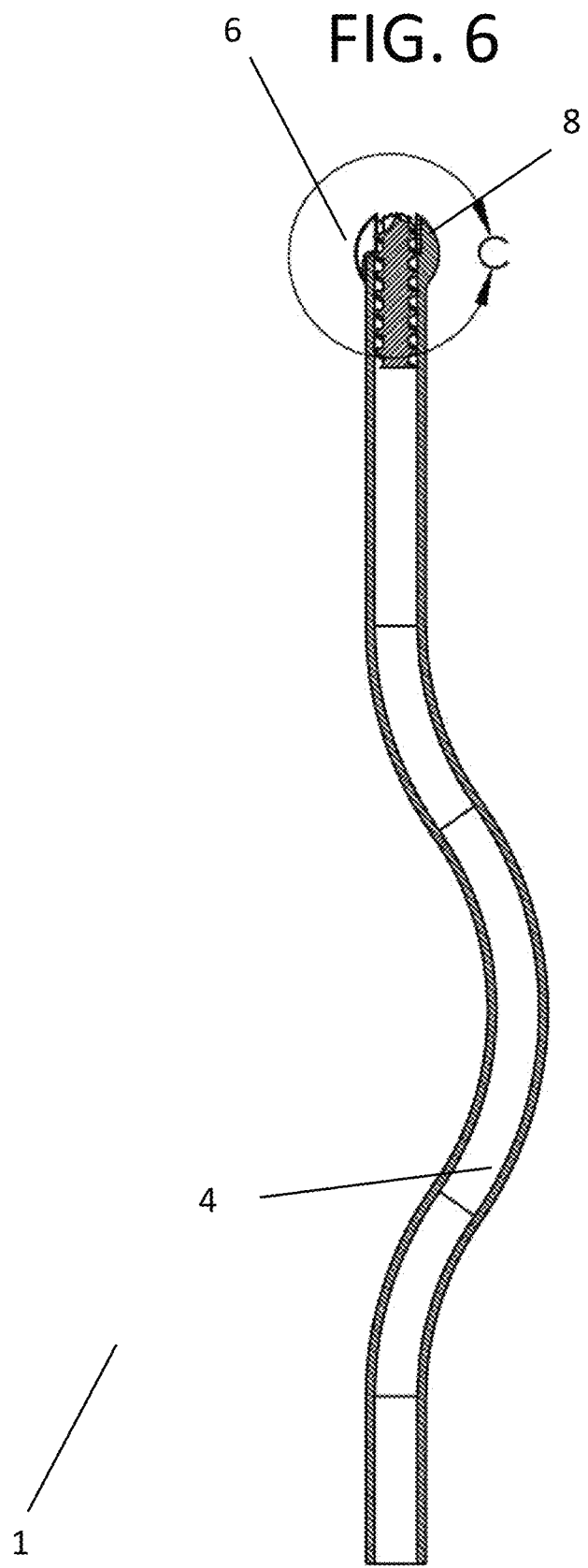
FIG. 6 illustrates a top view of the catheter atherector.
Figure 7:
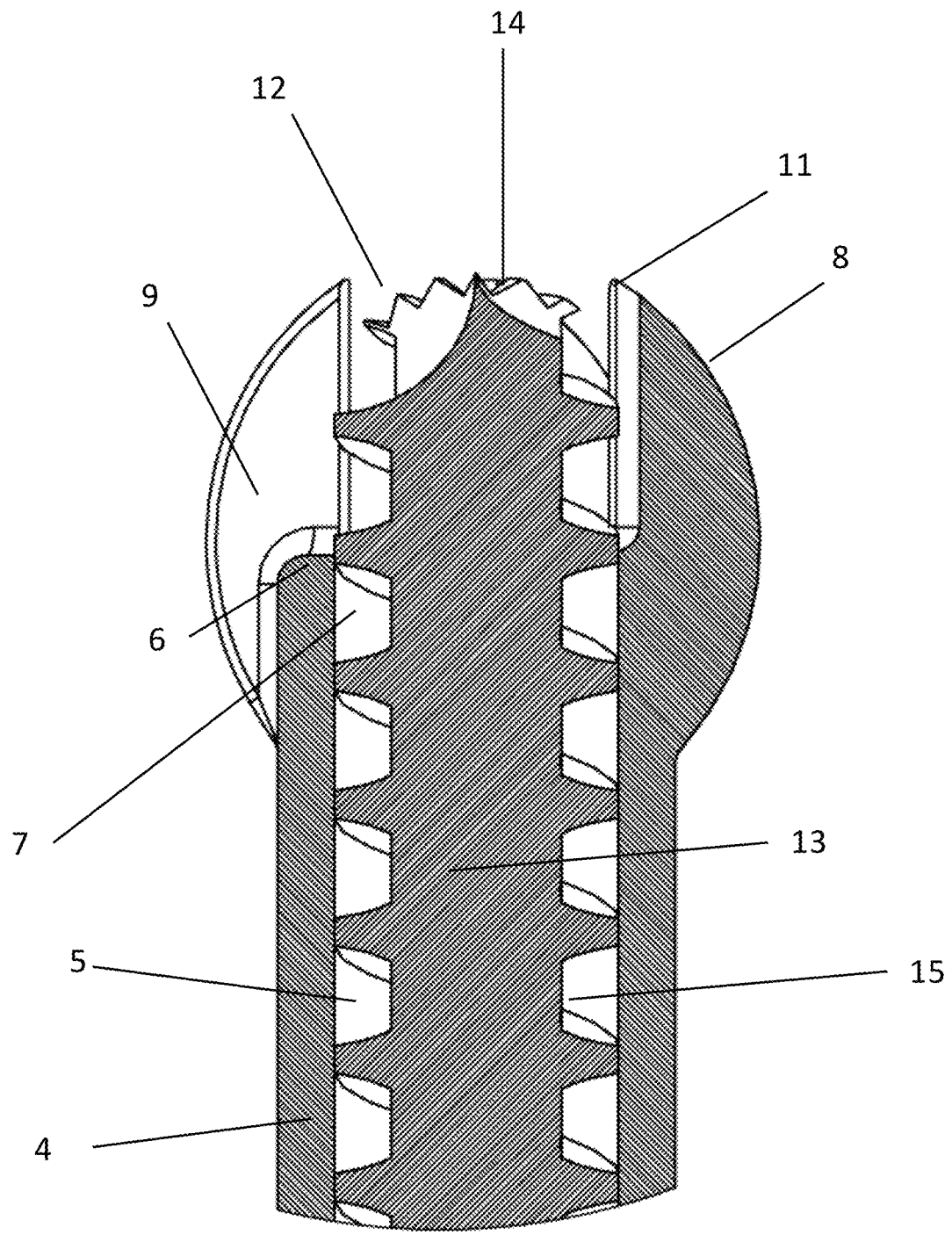
FIG. 7 illustrates a side cross-sectional view of the distal end of the catheter atherector.
Figure 8:
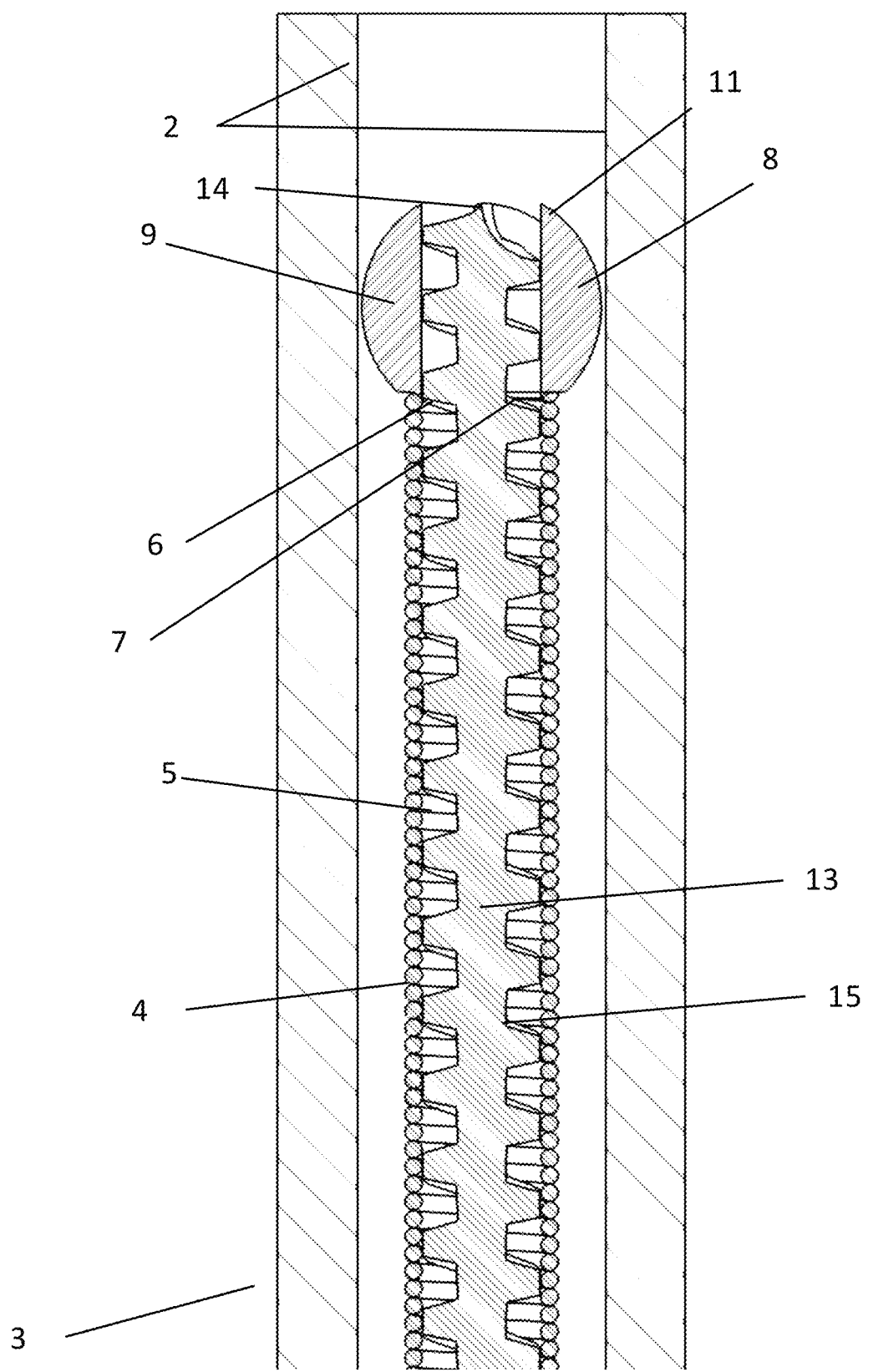
FIG. 8 illustrates another side cross-sectional view of the distal end of the catheter atherector.
Figure 9:
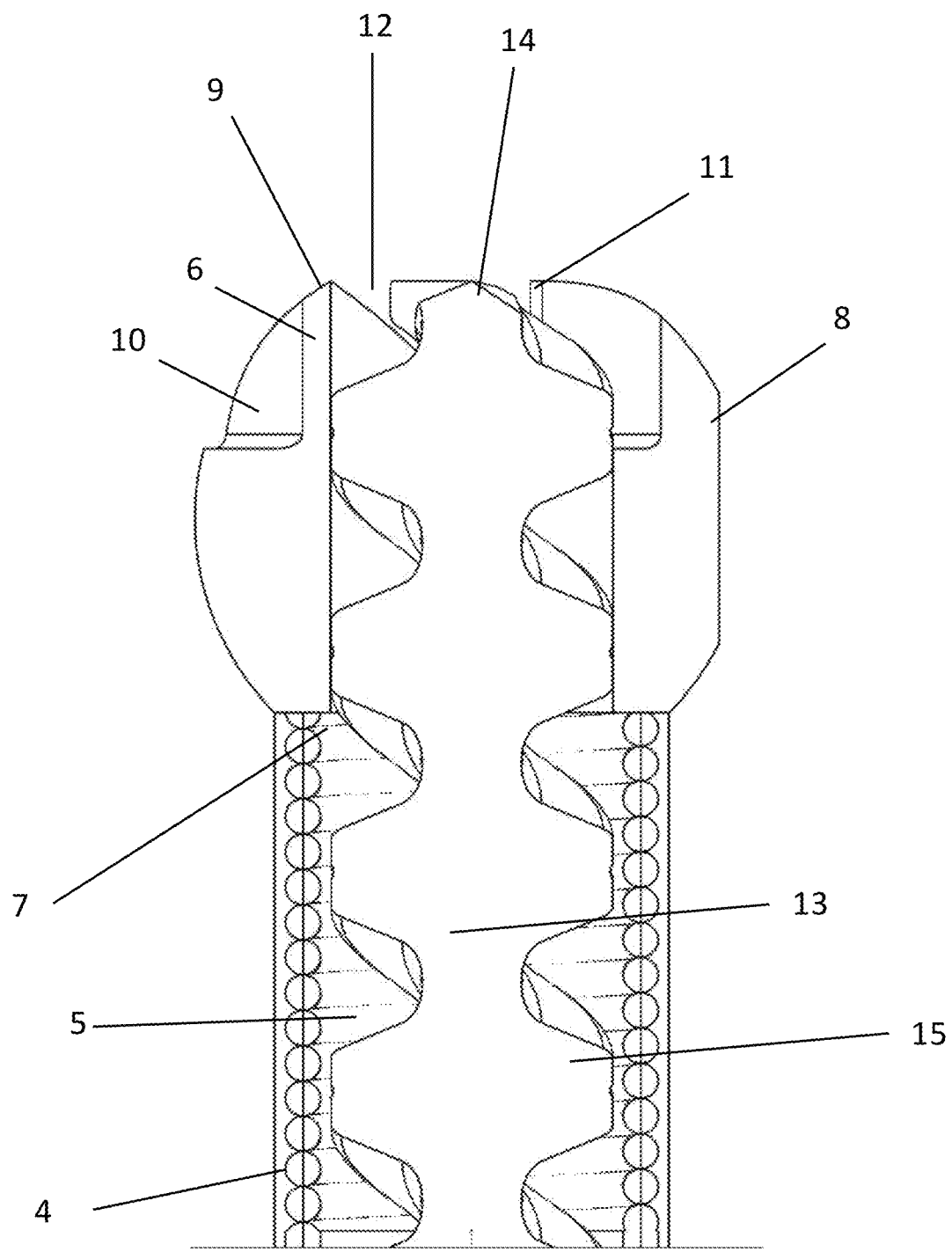
FIG. 9 illustrates a side cross-sectional view of the distal end of another embodiment of the catheter atherector.
Figure 10:
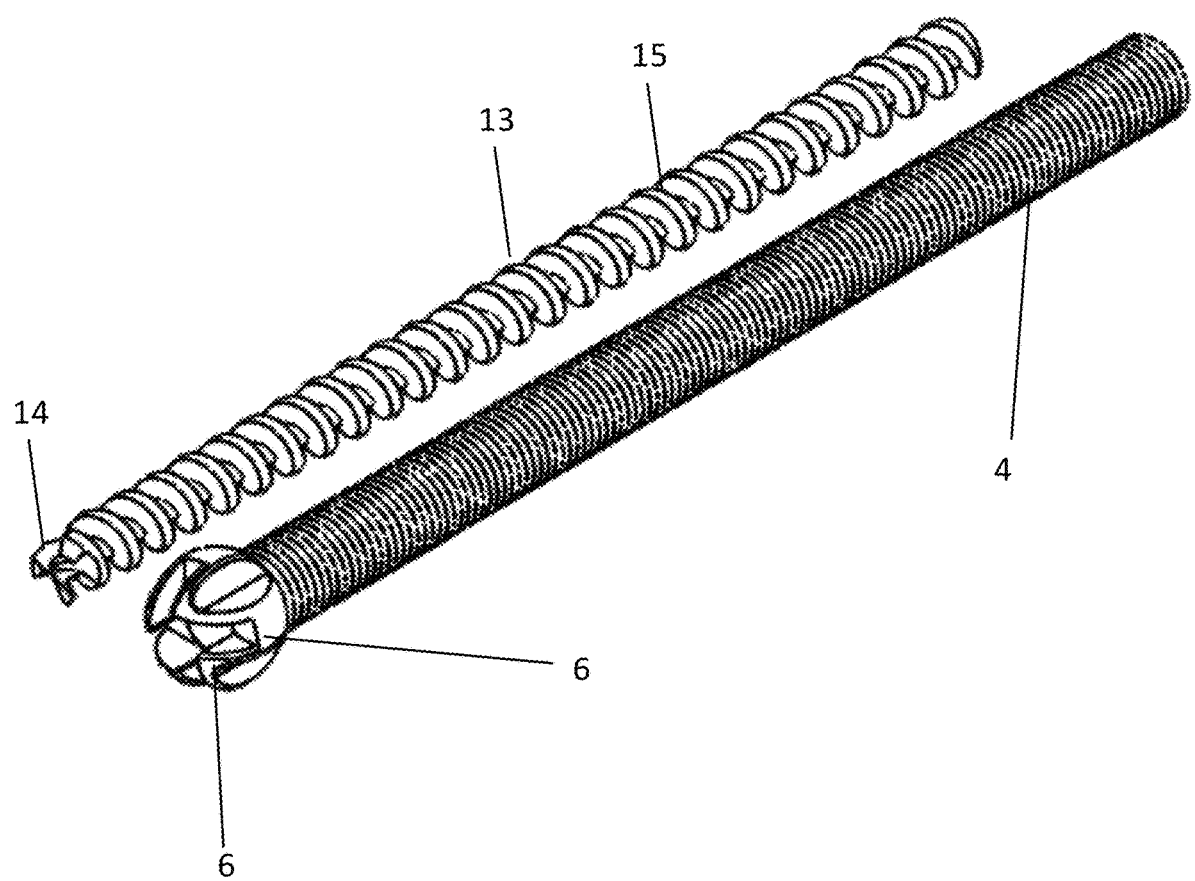
FIG. 10 illustrates a top isometric view of extraction wire and catheter of the catheter atherector.
Figure 11:
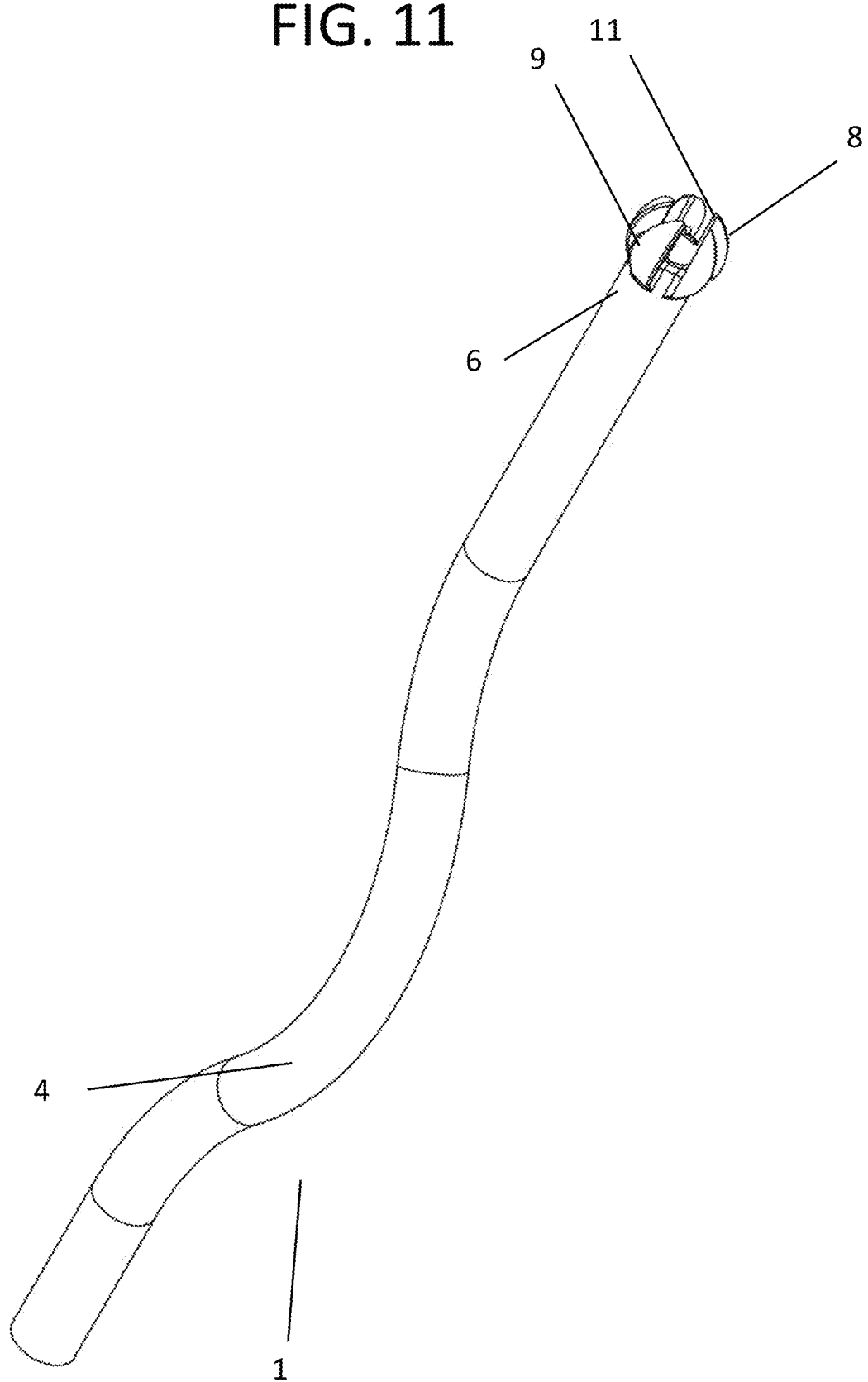
FIG. 11 illustrates a top isometric view of the catheter tubing.
Figure 12:
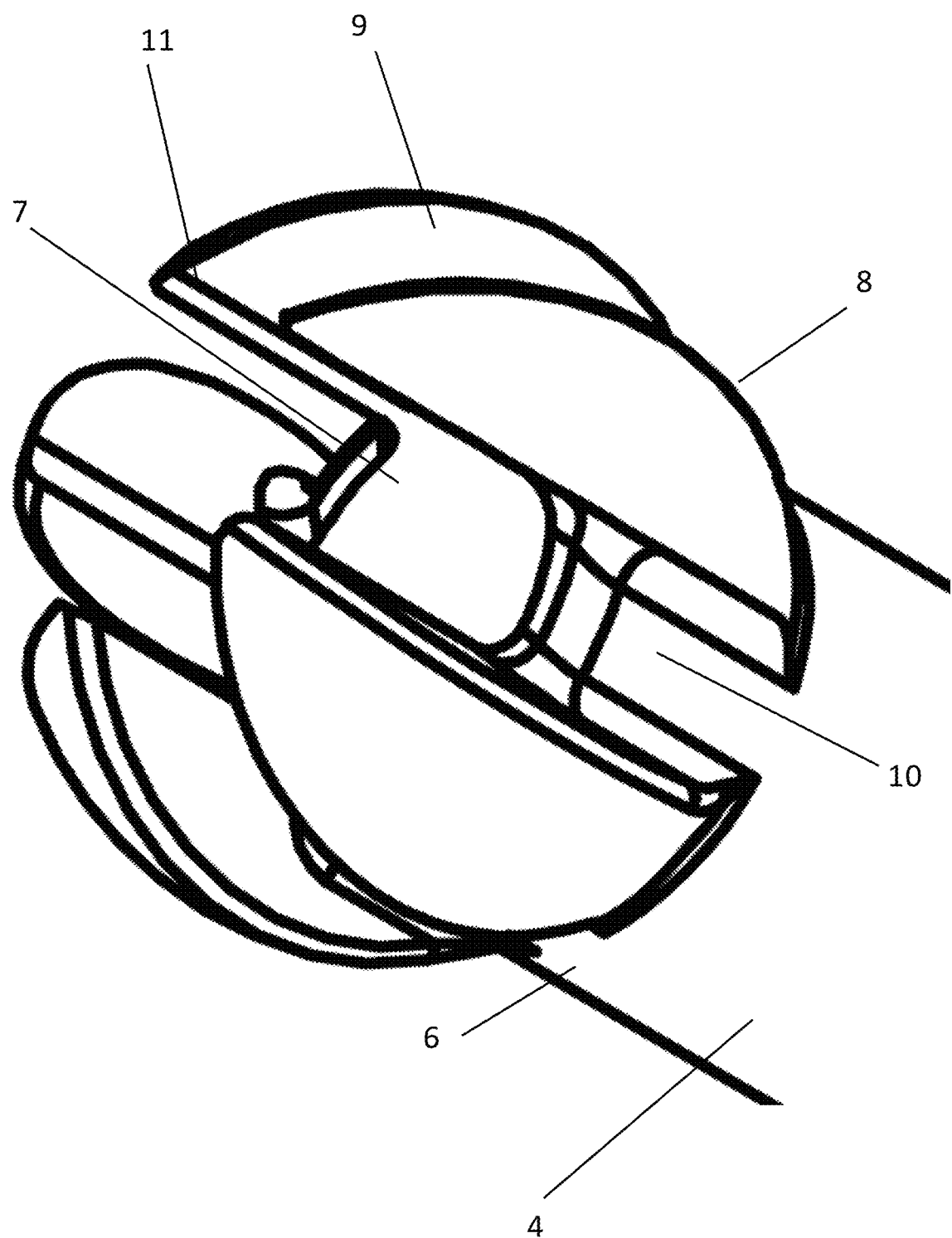
FIG. 12 illustrates a top isometric view of the distal end of the catheter tubing.
Figure 13:
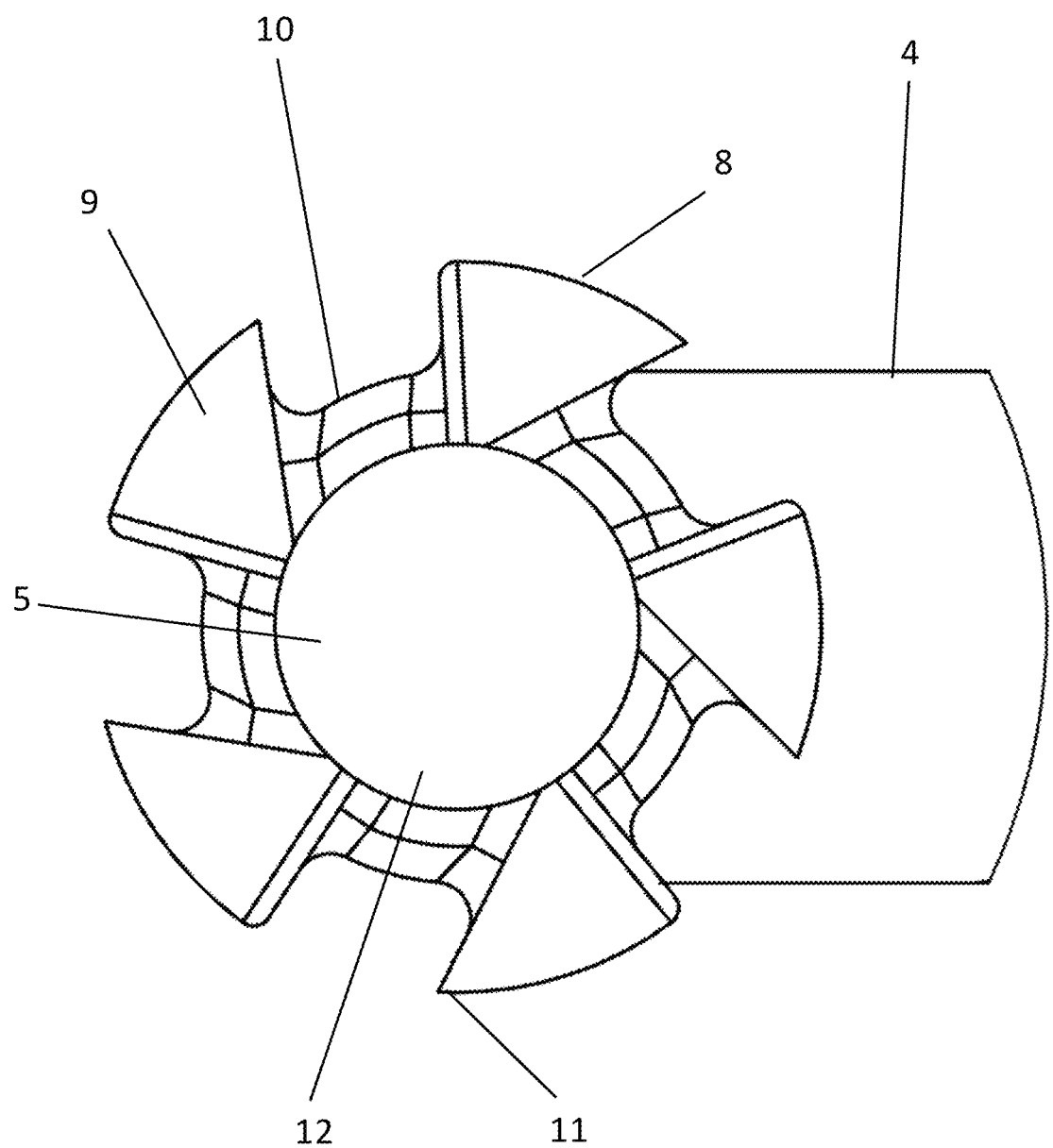
FIG. 13 illustrates a front view of the distal end of the catheter tubing.
Figure 14:
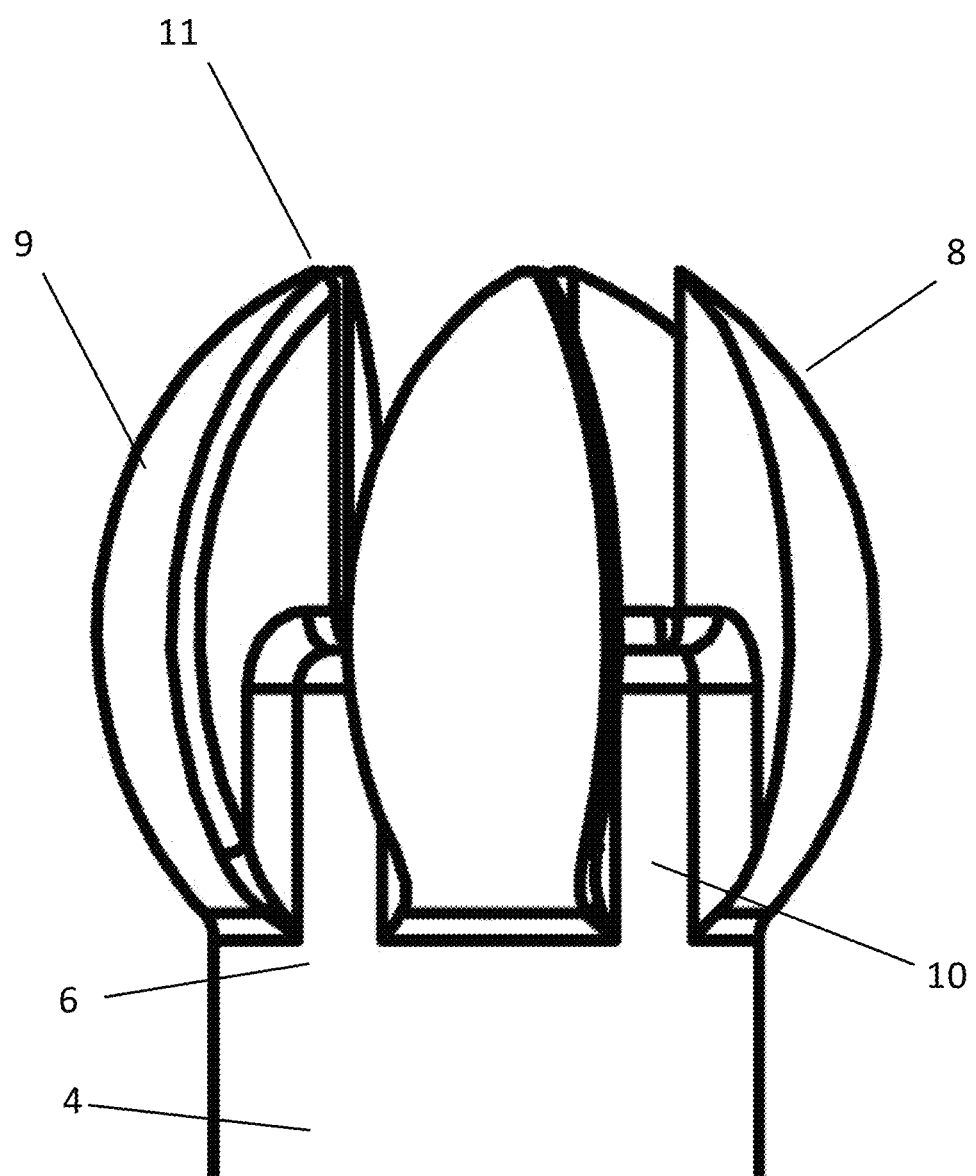
FIG. 14 illustrates a side view of the distal end of the catheter tubing.
Figure 15:
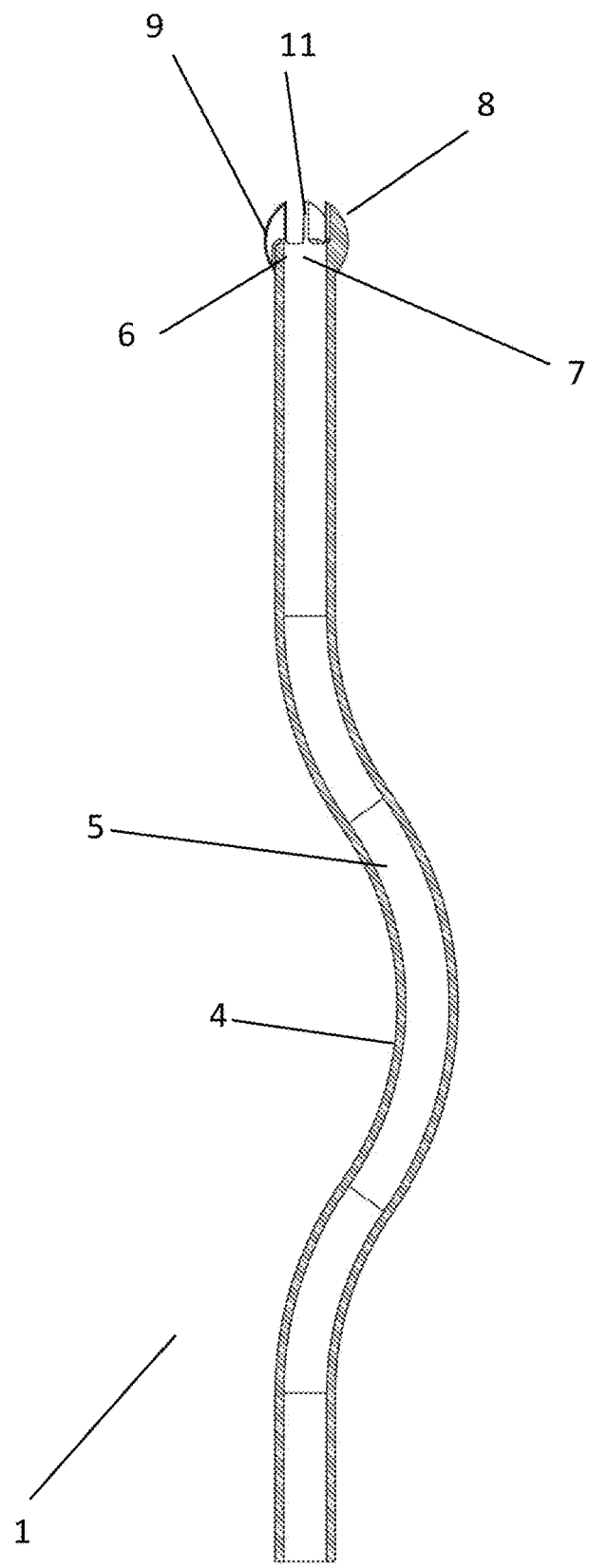
FIG. 15 illustrates a side cross-sectional view of the catheter tubing.
Figure 16:
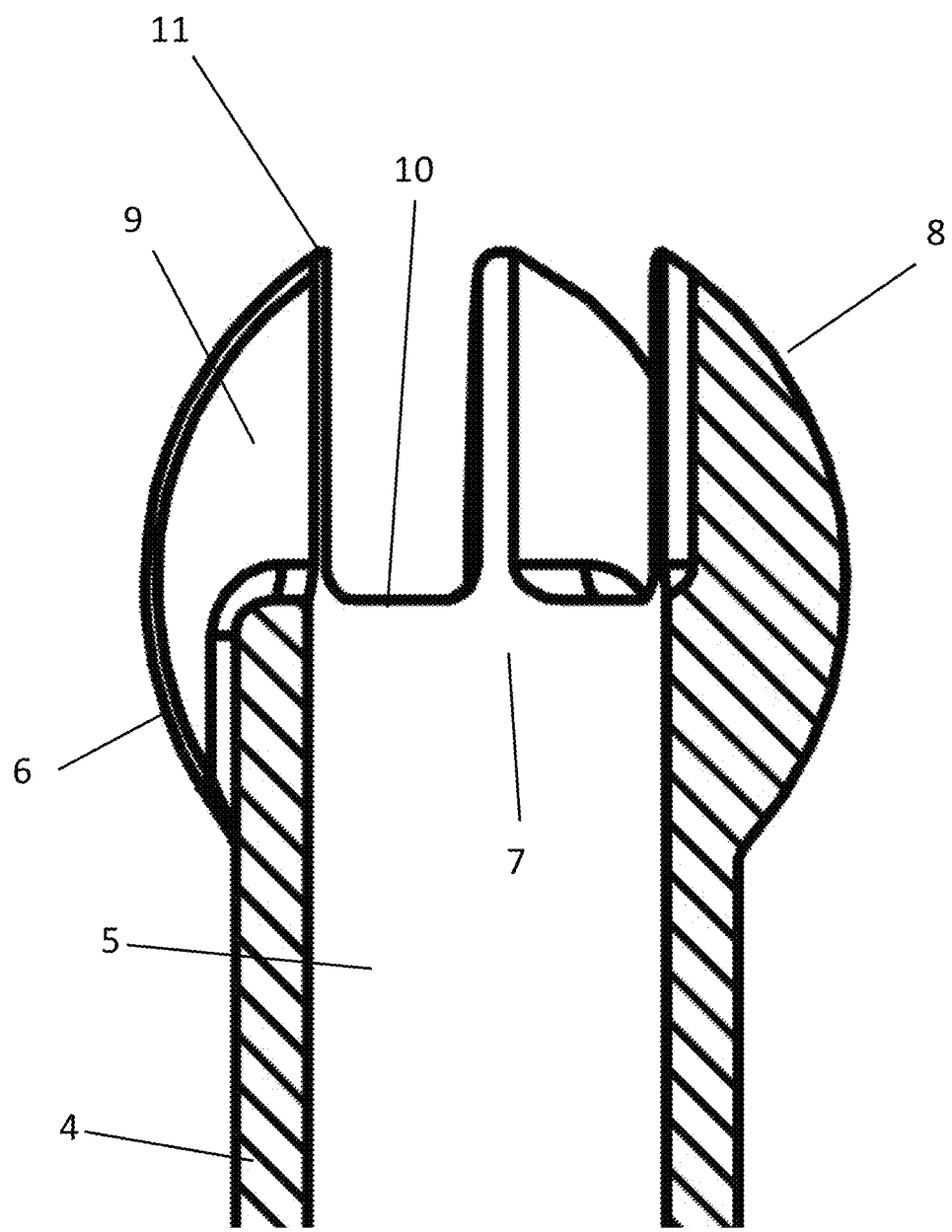
FIG. 16 illustrates a side view of the distal end of the catheter tubing.

While several variations of the present invention have been illustrated by way of example in particular embodiments, it is apparent that further embodiments could be developed within the spirit and scope of the present invention. However, it is to be expressly understood that such modifications and adaptations are within the spirit and scope of the present invention, and are inclusive, but not limited to the following appended claims as set forth.

As illustrated in FIGS. 1-15, the subject invention discloses a catheter atherector for use in minimally invasive intravascular plaque removal from inner walls 2 of blood vessels 3.

The catheter atherector 1 comprises a catheter 4 containing a hollow elongated lumen 5 with a distal end 6 with an opening 7 surrounded by a slotted emulsification reduction sphere 8. In embodiments of the subject invention, the catheter 4 has a diameter of 1 to 6 millimeters. The slotted emulsification reduction sphere 8 contains a plurality of curved protrusions 9 and slots 10. The emulsification reduction sphere 8 is expandable and retractable. In embodiments of the subject invention, the emulsification reduction sphere 8 has a diameter of 1.5 to 8 millimeters. In different embodiments of the subject invention, the emulsification reduction sphere 8 may be differently sized for different diameters of arteries. In additional embodiments of the subject invention, the curved protrusions 9 each comprise a width of 30% to 50% of the diameter of the emulsification reduction sphere 8. In further embodiments of the subject invention, the slots 10 each comprise a width of 10% to 50% of the diameter of the emulsification reduction sphere 8.

The curved protrusions 9 of the sphere 8 contain plaque-cutting distal tips 11. Due the size and spherical configuration of the plurality of protrusions 9, the plaque-cutting distal tips 11 cannot reach the inner walls 2 of the blood vessel 3 during operation of the catheter atherector 1, preventing any cutting or tearing of the inner walls 2 of the blood vessel 3, by the plaque-cutting distal tips 11. The outer surfaces of the protrusions 9 and slots 10 are substantially smooth and cannot cut or tear the inner walls 2 of the blood vessel 3.

The emulsification reduction sphere 8 contains an opening 12 into the catheter lumen 5, this opening 12 is formed within the plurality of curved protrusions 9, plaque-cutting distal tips 11, and slots 10.

An emulsification-extraction wire 13 is contained within the lumen 5 of catheter 4. The emulsification-extraction wire 13 has a cylindrical screw helical ridge body 15 to form an internal auger within the lumen 5 of catheter 4. The emulsification-extraction wire 13 cannot come into contact within inner walls 2 of the blood vessel 3, and thus cannot cut or tear them during operation of the catheter atherector 1.

The distal end of the emulsification-extraction wire 13 comprises sharp extending blades 14 that extend outward from the distal end 6 of the catheter 4 lumen 5 opening 7. These blades 14 are contained within the opening 12 of the emulsification reduction sphere 8 within the plurality of curved protrusions 9, plaque-cutting distal tips 11, and slots 10. The blades 14 do not extend past the plaque-cutting distal tips 11 of the emulsification reduction sphere 8, and thus cannot cut or tear the inner walls 2 of the blood vessel 3.

To insert the catheter atherector 1, a small incision is made on the patient, near the blood vessel 3 to be treated. The catheter atherector 1 is inserted into the blood vessel 3, and directed to the vessel wall 2 to be treated.

Once the catheter atherector 1 has reached the vessel wall 2 to be treated within the blood vessel 3, the emulsification reduction sphere 8 rotates, and moves axially back and forth, inside the vessel 3, to engage the accumulated plaque on the vessel wall 2. During this rotational and axial movement of the emulsification reduction sphere 8, the protrusions 9 of the emulsification reduction sphere 8 shave, shave and scoop, and dig accumulated plaque from the inner vessel wall 2. The plaque-cutting distal tips 11 of the protrusions 9 cut plaque into fine, reduced-size particles in front of the emulsification reduction sphere 8. Due to the size and spherical configuration of the plurality of protrusions 9, the plaque-cutting distal tips 11 do not contact, cut, tear, or pierce the inner walls 2 of the blood vessel 3 during operation of the catheter atherector 1, During operation, the substantially smooth outer surfaces of the protrusions 9 do not cut, tear, or pierce the inner walls 2 of the blood vessel 3. During operation, the substantially smooth outer surfaces of the protrusions 9 temporarily stretch the blood vessel 3, but do not permanently stretch the inner walls 2 of the blood vessel 3. In embodiments of the subject invention, the emulsification reduction sphere 8 rotates at a rate of 60 rpm to 300 rpm.

Once the catheter atherector 1 has reached the vessel wall 2 to be treated within the blood vessel 3, the emulsification-extraction wire 13 also rotates, and moves axially back and forth, inside the lumen 5 of catheter 4. The rotational and axial movement of the emulsification-extraction wire 13 is independent from the rotational and axial movement of the emulsification reduction sphere 8. The emulsification-extraction wire 13 rotates in an opposite rotational direction from the rotational movement of the emulsification reduction sphere 8. Due to the emulsification-extraction wire 13 being within the catheter 4 and the emulsification reduction sphere 8, the emulsification-extraction wire 13 and the extending blades 14 do not contact, cut, tear, or pierce the inner walls 2 of the blood vessel 3 during operation of the catheter atherector 1. In embodiments of the subject invention, the emulsification-extraction wire 13 rotates at a rate faster than the emulsification reduction sphere 8. In embodiments of the subject invention, the emulsification-extraction wire 13 rotates at a rate of 250 rpm and 800 rpm.

The sharp extending blades 14 that extend outward from the distal end 6 of the catheter on the emulsification-extraction wire 13 emulsify plaque removed from the vessel wall 2 by the emulsification reduction sphere 8.

Figure 17:
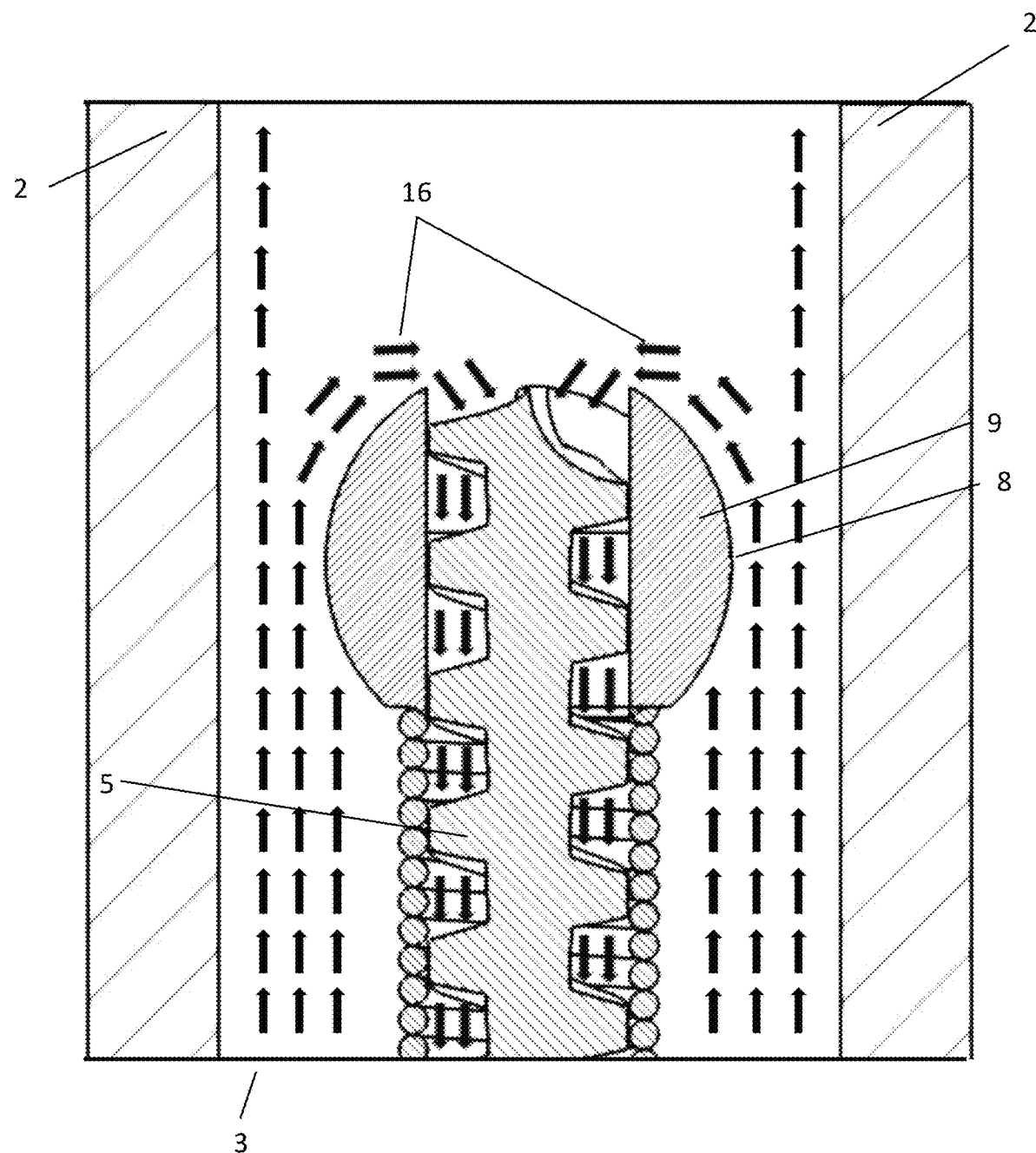
FIG. 17 illustrates a cross-sectional view of the distal end of the catheter atherector indicating blood flood during operation of the device.

As illustrated in FIG. 17, the mixture of blood and emulsified plaque flows 16 in a proximal direction into the catheter lumen 4 through vacuum suction, and can only move in the flowed 16 proximal direction on the cylindrical screw helical ridge body 15 internal auger within the lumen 5 of catheter 4. The mixture of blood 16 and emulsified plaque is filtered with a 10-micron filter, and blood flows back into the body of the patient. The emulsification reduction sphere 8 and the emulsification-extraction wire 13 allows blood 16 and emulsified plaque to flow 16 only in the direction of the 10-micron filter, not in the direction of the arterial system.

During the plaque emulsification process, laminar blood flow 16 within the blood vessel 3 is not stopped. Blood continues to flow 16 around the plurality of slots 10 on the emulsification reduction sphere 8 around the catheter 4 within the vessel walls 2. Blood also continues to flow through the 10 micron filter, and back into the patient. Operation of the catheter atherector 1 does not disrupt blood pressure within the blood vessel 3.

The invention claimed is:

1. A device configured to remove occlusive material from a vessel, comprising:
    a catheter with a hollow elongated lumen, a proximal opening, and a distal opening;
    an emulsification reduction of plaque particles sphere within the distal opening of the catheter, wherein the emulsification reduction of plaque particles sphere comprises a substantially spherical shape composed of a plurality of alternating, adjacent protrusions and slots, wherein each protrusion comprises a substantially smooth, curved surface extending outward, and a distal sharp tip, and each slot comprises a substantially smooth, curved sharp bottom surface extending inward;
    an opening on the emulsification reduction of plaque particles sphere into the distal opening of the catheter within the plurality of protrusions and slots;
    an emulsification-extraction wire contained within the lumen of catheter, wherein the emulsification-extraction wire comprises a substantially cylindrical screw helical ridge body and forms an internal auger within internal walls of the catheter lumen;
    a plurality of occlusive material cutters on the distal end of the emulsification-extraction wire extending outwardly from the distal opening of the catheter, wherein the plurality of occlusive material cutters are contained within the plurality of protrusions on the emulsification of plaque particles sphere;
    wherein the emulsification reduction of plaque particles sphere and the emulsification-extraction wire are configured to each independently rotate in opposite directions and move axially inside the vessel to engage the occlusive material;

wherein the plurality of protrustions shave and scoop the occlusive material into the plurality of occlusive material cutters for emulsification into reduced particles, and the plurality of protrusions are configured such that the movement of the plurality of protrusions does not pierce or cut the vessel wall;

wherein the distal sharp tips of each protrusion shave the occlusive material into the plurality of occlusive material particles for emulsification and distal sharp tips are configured to not contact the vessel wall; and wherein the mixture of emulsified occlusive material and blood only flows in a proximal direction into the catheter lumen through the plurality of occlusive material helical walls of the extraction wire cutters, wherein the mixture of emulsified occlusive material and blood is filtered and flows back into the vessel.

2. The device of claim 1, wherein the emulsification reduction of plaque particles sphere rotates at a rate of 60 rpm to 3000 rpm.

3. The device of claim 1, wherein the emulsification reduction of plaque particles sphere is expandable and retractable.

4. The device of claim 1, wherein the emulsification reduction of plaque particles sphere comprises a diameter of 1.5 to 8 millimeters.

5. The device of claim 1, wherein the rotational and axial movement of the emulsification-extraction wire is independent from the rotational and axial movement of the emulsification reduction of plaque particles sphere.

6. The device of claim 1, wherein the emulsification-extraction wire rotates at a rate faster than the emulsification reduction of plaque particles sphere.

7. The device of claim 1, wherein the emulsification-extraction wire rotates at a rate from 250 rpm to 8000 rpm.

8. The device of claim 1, wherein the plurality of alternating, adjacent protrusions on the emulsification reduction of plaque particles sphere each comprise a width of 30% to 50% of the diameter of the emulsification reduction of plaque particles sphere.

9. The device of claim 1, wherein the plurality of alternating, adjacent slots on the emulsification reduction of plaque particles sphere each comprise a width of 10% to 50% of the diameter of the emulsification reduction of plaque particles sphere.

10. A device configured to remove occlusive material from a vessel, comprising:
a catheter with a hollow elongated lumen, a proximal opening, and a distal opening;
a shaving and particles sphere within the distal opening of the guide catheter, wherein the shaving and particles sphere comprises a substantially spherical shape composed of a plurality of alternating, adjacent protrusions and slots, wherein each protrusion comprises a substantially smooth, curved surface extending outward, and distal sharp blades at the tip, and each slot comprises a substantially smooth, curved surface extending inward;
an opening on the shaving and particles sphere into the distal opening of the catheter within the plurality of protrusions and slots;
an emulsification-extraction wire contained within the lumen of catheter, wherein the emulsification-extraction wire comprises a substantially cylindrical screw helical ridged body and forms an internal auger within internal walls of the catheter lumen;
a plurality of occlusive material cutters on the distal end of the emulsification-extraction wire extending outwardly from the distal opening of the catheter, wherein the plurality of occlusive material cutters are contained within the plurality of protrusions on the shaving and particles sphere;

wherein the shaving and particles sphere and the emulsification-extraction wire are configured to each independently rotate and move axially inside the vessel to engage the occlusive material;

wherein the plurality of protrustions shave and scoop the occlusive material into the plurality of occlusive material slots for emulsification into reduced particles by sharp surfaces on the bottoms of the slots, and the plurality of protrusions are configured such that the movement of the plurality of protrusions does not pierce or cut the vessel wall;

wherein the distal sharp edges of each protrusion shave and cut the occlusive material into the plurality of occlusive material slots for emulsification and distal sharp edges and tips are configured to not contact the vessel wall;

wherein the mixture of emulsified occlusive material and blood only flows in a proximal direction into the catheter lumen through the plurality of occlusive material slots, wherein the mixture of emulsified occlusive material and blood is filtered and flows back into the vessel; and wherein during operation of the device, the device is configured such that laminar blood flow continues substantially uninterrupted in the blood vessel by flowing around the plurality of slots on the shaving and particles sphere and around the catheter within the vessel walls.

11. The device of claim 10, wherein the shaving and particles sphere rotates at a rate of 60 rpm to 3000 rpm.

12. The device of claim 10, wherein the shaving and particles sphere is expandable and retractable.

13. The device of claim 10, wherein the shaving and particles sphere comprises a diameter of 1.5 to 8 millimeters.

14. The device of claim 10, wherein the rotational and axial movement of the emulsification-extraction wire is independent from the rotational and axial movement of the shaving and particles sphere.

15. The device of claim 10, wherein the emulsification-extraction wire rotates at a rate faster than the shaving and particles sphere.

16. The device of claim 10, wherein the emulsification-extraction wire rotates at a rate from 250 rpm to 8000 rpm.

17. The device of claim 10, wherein the plurality of alternating, adjacent protrusions on the shaving and particles sphere each comprise a width of 30% to 50% of the diameter of the shaving and particles sphere.

18. The device of claim 10, wherein the plurality of alternating, adjacent slots on the shaving and particles sphere each comprise a width of 10% to 50% of the diameter of the shaving and particles sphere.

19. A device configured to remove occlusive material from a vessel, comprising:
a catheter with a hollow elongated lumen, a proximal opening, and a distal opening;
an emulsification reduction sphere within the distal opening of the catheter, wherein the emulsification reduction sphere comprises a substantially spherical shape composed of a plurality of alternating, adjacent protrusions and slots, wherein each protrusion comprises a substantially smooth, curved surface extending outward, and a distal sharp edges and tip, and each slot comprises a substantially smooth, curved surface extending inward;

an opening on the emulsification reduction sphere into the distal opening of the catheter within the plurality of protrusions and slots; an emulsification-extraction wire contained within the lumen of catheter, wherein the emulsification-extraction wire comprises a substantially cylindrical screw helical ridge body and forms an internal auger within internal walls of the catheter lumen;

a plurality of occlusive material cutters on the distal end of the emulsification-extraction wire extending outwardly from the distal opening of the catheter, wherein the plurality of occlusive material cutters are contained within the plurality of protrusions on the emulsification sphere;

wherein the emulsification reduction sphere and the emulsification-extraction wire are configured to each independently rotate in opposite directions and together move axially inside the vessel to engage the occlusive material;

wherein the plurality of protrusions shave and scoop the occlusive material into the plurality of occlusive material cutters for emulsification and the plurality of protrusions are configured such that the movement of the plurality of protrusions does not pierce or cut the vessel wall;

wherein the distal sharp tips of each protrusion cut the occlusive material into the plurality of occlusive material cutters for emulsification and distal sharp tips are configured to not contact the vessel wall;

wherein the mixture of emulsified occlusive material and blood only flows in a proximal direction into the catheter lumen through the plurality of occlusive material cutters, wherein the mixture of emulsified occlusive material and blood is filtered and flows back into the vessel; and wherein during operation of the device, the device is configured such that it does not substantially disrupt blood flow and pressure within the blood vessel.

\* \* \* \* \*